United States Patent
Galabura et al.

(10) Patent No.: US 12,194,435 B2
(45) Date of Patent: Jan. 14, 2025

(54) NANOPOROUS SUPERABSORBENT PARTICLES

(71) Applicant: Kimberly-Clark Worldwide, Inc., Neenah, WI (US)

(72) Inventors: Yuriy Galabura, Appleton, WI (US); Austin N. Pickett, Menasha, WI (US); Karen Goeders, Alpharetta, GA (US); Vasily A. Topolkaraev, Appleton, WI (US); Dave Soerens, Neenah, WI (US); Theodore T. Tower, Appleton, WI (US); Mark M. Mleziva, Appleton, WI (US); WanDuk Lee, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 979 days.

(21) Appl. No.: 16/631,553

(22) PCT Filed: Jul. 20, 2018

(86) PCT No.: PCT/US2018/043095
§ 371 (c)(1),
(2) Date: Jan. 16, 2020

(87) PCT Pub. No.: WO2019/023060
PCT Pub. Date: Jan. 31, 2019

(65) Prior Publication Data
US 2020/0171462 A1 Jun. 4, 2020

Related U.S. Application Data
(60) Provisional application No. 62/537,999, filed on Jul. 28, 2017.

(51) Int. Cl.
*B01J 20/26* (2006.01)
*B01J 20/28* (2006.01)
*B01J 20/30* (2006.01)

(52) U.S. Cl.
CPC ....... *B01J 20/267* (2013.01); *B01J 20/28004* (2013.01); *B01J 20/28011* (2013.01);
(Continued)

(58) Field of Classification Search
CPC ............... B01J 20/267; B01J 20/28004; B01J 20/28011; B01J 20/28016; B01J 20/28059;
(Continued)

(56) References Cited

U.S. PATENT DOCUMENTS 3,957,651 A 5/1976 Kesting
4,057,669 A 11/1977 McConnell
(Continued)

FOREIGN PATENT DOCUMENTS

BR PI0904295 6/2011
CA 1120670 3/1982
(Continued)

OTHER PUBLICATIONS

Chinese Office Action Corresponding to Application No. 201880049766 on Jun. 7, 2022.
(Continued)

*Primary Examiner* — Jeffrey D Washville
(74) *Attorney, Agent, or Firm* — Dority & Manning, P.A.

(57) ABSTRACT

Superabsorbent particles having a median size of from about 50 to about 2,000 micrometers and containing nanopores having an average cross-sectional dimension of from about 10 to about 500 nanometers are provided. The superabsorbent particles exhibit a Vortex Time of about 80 seconds or less.

25 Claims, 8 Drawing Sheets

(52) U.S. Cl.
CPC ... *B01J 20/28016* (2013.01); *B01J 20/28059* (2013.01); *B01J 20/2808* (2013.01); *B01J 20/28083* (2013.01); *B01J 20/28085* (2013.01); *B01J 20/28092* (2013.01); *B01J 20/3071* (2013.01)

(58) Field of Classification Search
CPC .............. B01J 20/2808; B01J 20/28083; B01J 20/28085; B01J 20/28092; B01J 20/3071; A61F 2013/530481; A61F 2013/530569; A61F 2013/530591; A61F 13/53; A61L 15/60; A61L 15/24; A61L 2400/12
USPC ....... 502/150, 159, 162, 164, 167, 168, 400, 502/401, 402, 411
See application file for complete search history.

(56) References Cited

U.S. PATENT DOCUMENTS

| | | |
|---|---|---|
| 4,076,663 A | 2/1978 | Masuda et al. |
| 4,100,324 A | 7/1978 | Anderson et al. |
| 4,286,082 A | 8/1981 | Tsubakimoto et al. |
| 4,340,706 A | 7/1982 | Obayashi et al. |
| 4,497,930 A | 2/1985 | Yamasaki et al. |
| 4,507,438 A | 3/1985 | Obayashi et al. |
| 4,654,039 A | 3/1987 | Brandt et al. |
| 4,666,975 A | 5/1987 | Yamasaki et al. |
| 4,683,274 A | 7/1987 | Nakamura et al. |
| 4,704,116 A | 11/1987 | Enloe |
| 4,798,603 A | 1/1989 | Meyer et al. |
| 4,801,494 A | 1/1989 | Datta et al. |
| 4,908,026 A | 3/1990 | Sukiennik et al. |
| 5,145,906 A | 9/1992 | Chambers et al. |
| 5,192,606 A | 3/1993 | Oda et al. |
| 5,248,309 A | 9/1993 | Serbiak et al. |
| 5,350,624 A | 9/1994 | Georger et al. |
| 5,405,666 A | 4/1995 | Brindle |
| 5,415,640 A | 5/1995 | Kirby et al. |
| 5,486,166 A | 1/1996 | Bishop et al. |
| 5,490,846 A | 2/1996 | Ellis et al. |
| 5,494,940 A | 2/1996 | Unger |
| 5,498,478 A | 3/1996 | Hansen |
| 5,508,102 A | 4/1996 | Georger et al. |
| 5,560,878 A | 10/1996 | Dragoo et al. |
| 5,702,377 A | 12/1997 | Collier et al. |
| 5,814,673 A | 9/1998 | Khait |
| 5,888,231 A | 3/1999 | Sandvig et al. |
| 5,931,823 A | 8/1999 | Stokes et al. |
| 5,973,014 A | 10/1999 | Funk et al. |
| 6,019,996 A | 2/2000 | Cheong |
| 6,060,638 A | 5/2000 | Paul et al. |
| 6,071,406 A | 6/2000 | Tsou |
| 6,143,211 A | 11/2000 | Mathiowitz et al. |
| 6,150,002 A | 11/2000 | Varona |
| 6,222,091 B1 | 4/2001 | Beihoffer et al. |
| 6,376,618 B1 | 4/2002 | Mitchell et al. |
| 6,431,477 B1 | 8/2002 | Pallmann |
| 6,479,003 B1 | 11/2002 | Furgiuele et al. |
| 6,494,390 B1 | 12/2002 | Khait et al. |
| 6,573,305 B1 | 6/2003 | Thunhorst et al. |
| 6,663,611 B2 | 12/2003 | Blaney et al. |
| 6,689,465 B1 | 2/2004 | Omori et al. |
| 6,720,073 B2 | 4/2004 | Lange et al. |
| 6,737,491 B2 | 5/2004 | Soerens et al. |
| 6,818,173 B1 | 11/2004 | Khait et al. |
| 6,849,672 B2 | 2/2005 | Mehawej et al. |
| 6,939,914 B2 | 9/2005 | Qin et al. |
| 6,960,617 B2 | 11/2005 | Omidian et al. |
| 7,056,957 B2 | 6/2006 | Omidian et al. |
| 7,265,192 B2 | 9/2007 | Soerens et al. |
| 7,288,317 B2 | 10/2007 | Poulin et al. |
| 7,396,584 B2 | 7/2008 | Azad et al. |
| 7,510,133 B2 | 3/2009 | Pallmann |
| 7,777,095 B2 | 8/2010 | Soerens |
| 7,988,992 B2 | 8/2011 | Omidian et al. |
| 8,021,998 B2 | 9/2011 | Qin et al. |
| 8,138,281 B2 | 3/2012 | Weismantel et al. |
| 8,383,877 B2 | 2/2013 | Singh Kainth et al. |
| 8,742,023 B2 | 6/2014 | Fujimura et al. |
| 9,078,946 B2 | 7/2015 | Badri et al. |
| 2003/0003830 A1 | 1/2003 | Ouederni et al. |
| 2003/0130639 A1 | 7/2003 | Ishikawa et al. |
| 2003/0200991 A1 | 10/2003 | Keck et al. |
| 2004/0019166 A1 | 1/2004 | Soerens et al. |
| 2004/0067214 A1 | 4/2004 | Krautkramer et al. |
| 2004/0092658 A1 | 5/2004 | Qin et al. |
| 2004/0102750 A1 | 5/2004 | Jameson |
| 2005/0054255 A1 | 3/2005 | Morman et al. |
| 2005/0059941 A1 | 3/2005 | Baldwin et al. |
| 2005/0288641 A1 | 12/2005 | Sorens |
| 2006/0178465 A9 | 8/2006 | Torkelson et al. |
| 2007/0049153 A1 | 3/2007 | Dunbar et al. |
| 2007/0049888 A1 | 3/2007 | Soerens et al. |
| 2008/0022940 A1 | 1/2008 | Kirsch et al. |
| 2008/0058747 A1 | 3/2008 | Singh et al. |
| 2008/0227944 A1 | 9/2008 | Ambrosio et al. |
| 2010/0261812 A1 | 10/2010 | Qin et al. |
| 2010/0266794 A1 | 10/2010 | Wright et al. |
| 2011/0275513 A1 | 11/2011 | Tian et al. |
| 2011/0301560 A1 | 12/2011 | Fujimura et al. |
| 2012/0219728 A1 | 8/2012 | Badri et al. |
| 2013/0030340 A1 | 1/2013 | Vincent et al. |
| 2013/0037481 A1 | 2/2013 | Lalouch et al. |
| 2013/0089737 A1 | 4/2013 | Sannino et al. |
| 2013/0172509 A1 | 7/2013 | Pawloski et al. |
| 2014/0296507 A1 | 10/2014 | Sannino et al. |
| 2014/0309607 A1 | 10/2014 | Richlen et al. |
| 2015/0190543 A1 | 1/2015 | Marshall et al. |
| 2015/0157759 A1 | 6/2015 | Azad et al. |
| 2015/0342799 A1 | 12/2015 | Michiels et al. |
| 2016/0101208 A1 | 4/2016 | Topolkaraev et al. |
| 2016/0168349 A1 | 6/2016 | Topolkaraev et al. |
| 2016/0354757 A1 | 12/2016 | Lee et al. |
| 2017/0079854 A1 | 3/2017 | Butler et al. |
| 2017/0216817 A1 | 8/2017 | Torii et al. |
| 2018/0043332 A1 | 2/2018 | Lee et al. |
| 2018/0194904 A1* | 7/2018 | Lee .................. C08F 20/56 |

FOREIGN PATENT DOCUMENTS

| | | |
|---|---|---|
| CN | 102197057 A | 9/2011 |
| CN | 104107681 | 10/2014 |
| CN | 10455317 A | 4/2015 |
| CN | 105451722 A | 3/2016 |
| CN | 108026284 A | 5/2018 |
| EP | 1178843 | 2/2002 |
| EP | 2740747 | 6/2014 |
| GB | 1102342 | 2/1968 |
| GB | 1174959 | 12/1969 |
| JP | H01292003 | 11/1989 |
| JP | H02194010 | 7/1990 |
| JP | H0364301 | 3/1991 |
| JP | 2006342306 | 12/2006 |
| JP | 2013252330 | 12/2013 |
| JP | 2013252331 | 12/2013 |
| KR | 20100014556 A | 2/2010 |
| KR | 100947302 | 3/2010 |
| KR | 20170068383 A | 6/2017 |
| KR | 1020170063818 | 6/2017 |
| KR | 1020170075624 | 7/2017 |
| KR | 1020170075643 | 7/2017 |
| KR | 20200036604 A | 4/2020 |
| RU | 2091081 C1 | 9/1997 |
| RU | 2577268 C2 | 3/2010 |
| RU | 2010138539 | 3/2012 |
| RU | 2622431 C1 | 6/2017 |
| RU | 2637223 C2 | 12/2017 |
| RU | 2725578 C2 | 7/2020 |
| RU | 2752620 C2 | 7/2021 |
| WO | WO9512632 | 5/1995 |
| WO | WO2005063313 | 7/2005 |
| WO | WO2005/120594 A1 | 12/2005 |
| WO | WO2009022358 | 2/2009 |

(56) References Cited

FOREIGN PATENT DOCUMENTS

| WO | WO2011063372 | 5/2011 |
|---|---|---|
| WO | WO2015/051364 A1 | 4/2015 |
| WO | WO2016053830 A1 | 4/2016 |
| WO | WO2017/111295 A1 | 6/2017 |

OTHER PUBLICATIONS

Buchholz et al., Wily-VCH, Modern Superabsorbent Polymer Technology, 1998.
International Search Report and Written Opinion for PCT/US2018/043095 dated Jan. 2, 2019, 12 pages.
Third Party Observation for PCT/US2018/043095 dated Nov. 20, 2019, 10 pages.
Udoh et al., "Microporous Polymer Particles via Phase Inversion in Microfluidics: Impact of Nonsolvent Quality", American Chemical Society, Langmuir Jul. 22, 2016, 32 (32), pp. 8131-8140.
Russian Office Action Corresponding to Application No. 2020141573 on May 18, 2021.
Chinese Office Action Corresponding to Application No. 201880093564 on Mar. 30, 2021.
Shou D. et al. Optimal Design of Porous Structures for the Fastest Liquid Absorption // Langmuir, 2014, V. 30, pp. 149-155 (Abstract Only).
Koroleva M.Y. et al. Nanoemulsions: properties, methods of preparation and promising areas of application // Uspekhi Khimii (Russian Chemical Reviews), 2012, vol. 81, pp. 21-43 (Abstract Only).
Pourjavadi A. et al. Preparation and swelling behaviour of a novel anti-salt superabsorbent hydrogel based on kappa-carrageenan and sodium alginate grafted with polyacrylamide // EPolymers, 2004, V.4, pp. 1-13.
Chinese Office Action Corresponding to Application No. 201880049766 on Aug. 24, 2021.
Russian Office Action Corresponding to Application No. 2020105297 on Nov. 8, 2021.
Machine Translated Korean Office Action Corresponding to Application No. 1020217000382 on Mar. 15, 2021.

* cited by examiner

NANOPOROUS SUPERABSORBENT PARTICLES

RELATED APPLICATIONS

The present application is the national stage entry of International Patent Application No. PCT/US2018/043095 having a filing date of Jul. 20, 2018, which claims priority to U.S. Provisional Application Ser. No. 62/537,999 having a filing date of Jul. 28, 2017, both of which are incorporated herein in their entirety by reference thereto.

BACKGROUND OF THE INVENTION

Superabsorbent materials are employed in a wide variety of applications to help absorb fluids. These materials are generally capable of absorbing a fluid (e.g., water, saline, etc.) in an amount several times their own weight. Still, one problem associated with many conventional superabsorbent materials is that when they initially come into contact with the fluid, the rate of absorption can be relatively slow. As such, a need currently exists for a superabsorbent material that exhibits relatively fast absorption rates, particularly when initially coming into contact with a fluid.

SUMMARY OF THE INVENTION

In accordance with one embodiment of the present invention, superabsorbent particles are disclosed that have a median size of from about 50 to about 2,000 micrometers and contains nanopores having an average cross-sectional dimension of from about 10 to about 500 nanometers. The superabsorbent particles exhibit a Vortex Time of about 80 seconds or less.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
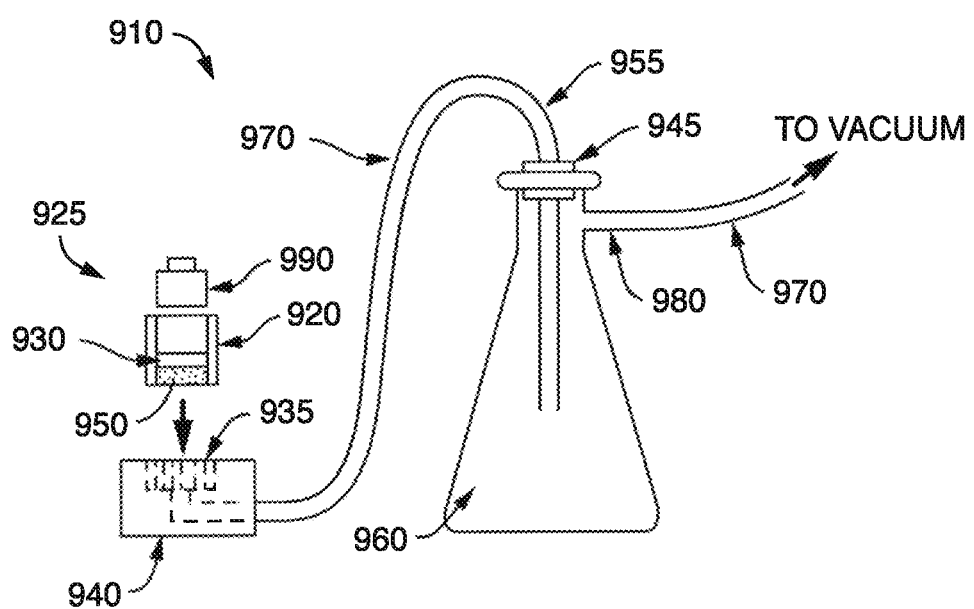
FIG. 1 depicts an apparatus that can be used to measure absorbency under load ("AUL") of the porous superabsorbent particles of the present invention.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to superabsorbent particles, which typically have a median size (e.g., diameter) of from about 50 to about 2,000 micrometers, in some embodiments from about 100 to about 1,000 micrometers, and in some embodiments, from about 200 to about 700 micrometers. The term "median" size as used herein refers to the "D50" size distribution of the particles, which means that at least 50% of the particles have the size indicated. The particles may likewise have a D90 size distribution (at least 90% of the particles have the size indicated) within the ranges noted above. The diameter of particles may be determined using known techniques, such as by ultracentrifuge, laser diffraction, etc. For example, particle size distribution can be determined according to a standard testing method such as ISO 13320:2009. The particles may also possess any desired shape, such as flake, nodular, spherical, tube, etc. The size of the particles may be controlled to optimize performance for a particular application. The specific surface area of the particles may also be relatively large, such as about 0.2 square meters per gram ($m^2/g$) or more, in some embodiments about 0.6 $m^2/g$ or more, and in some embodiments, from about 1 $m^2/g$ to about 5 $m^2/g$, such as determined in accordance with the B. E. T. test method as described in ISO 9277:2010.

Regardless of their particular size or shape, the superabsorbent particles are porous in nature and generally possess a porous network, which may contain a combination of closed and open-celled pores. The total porosity of the particles may be relatively high. For example, the particles may exhibit a total pore area of about 2 square meters per gram ($m^2/g$) or more, in some embodiments from about 5 to about 150 $m^2/g$, and in some embodiments, from about 15 to about 40 $m^2/g$. The percent porosity may also be about 5% or more, in some embodiments from about 10% to about 60%, and in some embodiments, from about 15% to about 60%. Another parameter that is characteristic of porosity is bulk density. In this regard, the bulk density of the superabsorbent particles of the present invention may, for example, be less than about 0.7 grams per cubic centimeter ($g/cm^3$), in some embodiments from about 0.1 to about 0.65 $g/cm^3$, and in some embodiments, from about 0.2 to about 0.6 $g/cm^3$, as determined at a pressure of 0.58 psi via mercury intrusion.

To achieve the desired pore properties, the porous network typically contains a plurality of nanopores having an average cross-sectional dimension (e.g., width or diameter) of from about 10 to about 500 nanometers, in some embodiments from about 15 to about 450 nanometers, and in some embodiments, from about 20 to about 400 nanometers. The term "cross-sectional dimension" generally refers to a characteristic dimension (e.g., width or diameter) of a pore, which is substantially orthogonal to its major axis (e.g., length). It should be understood that multiple types of pores may exist within the network. For example, micropores may also be formed that have an average cross-sectional dimension of from about 0.5 to about 30 micrometers, in some embodiments from about 1 to about 20 micrometers, and in some embodiments, from about 2 micrometers to about 15 micrometers. Nevertheless, nanopores can be present in a relatively high amount in the network. For example, the nanopores may constitute at least about 25 vol. %, in some embodiments at least about 40 vol. %, and in some embodiments, from about 40 vol. % to 80 vol. % of the total pore volume of the particles. The average percent volume occupied by the nanopores within a given unit volume of the material may also be from about 15% to about 80% per cm$^3$, in some embodiments from about 20% to about 70%, and in some embodiments, from about 30% to about 60% per cubic centimeter of the particles. Multiple subtypes of nanopores may also be employed. In certain embodiments, for instance, first nanopores may be formed that have an average cross-sectional dimension of from about 80 to about 500 nanometers, in some embodiments from about 90 to about 450 nanometers, and in some embodiments, from about 100 to about 400 nanometers, while second nanopores may be formed that have an average cross-sectional dimension of from about 1 to about 80 nanometers, in some embodiments from about 5 to about 70 nanometers, and in some embodiments from about 10 to about 60 nanometers. The nanopores may have any regular or irregular shape, such as spherical, elongated, etc. Regardless, the average diameter of the pores within the porous network will typically be from about 1 to about 1,200 nanometers, in some embodiments from about 10 nanometers to about 1,000 nanometers, in some embodiments from about 50 to about 800 nanometers, and in some embodiments, from about 100 to about 600 nanometers.

Due in part to the particular nature of the porous network, the present inventors have discovered that the resulting superabsorbent particles can exhibit an enhanced rate of absorption during the specific time period in which they begin to contact a fluid, such as water, aqueous solutions of a salt (e.g., sodium chloride), bodily fluids (e.g., urine, blood, etc.), and so forth. This increased rate can be characterized in a variety of ways. For example, the particles may exhibit a low Vortex Time, which refers to the amount of time in seconds required for an amount of the superabsorbent particles to close a vortex created by stirring an amount of 0.9 percent (%) by weight sodium chloride solution according to the test described below. More particularly, the superabsorbent particles may exhibit a Vortex Time of about 80 seconds or less, in some embodiments about 60 seconds or less, in some embodiments about 45 seconds or less, in some embodiments about 35 seconds or less, in some embodiments about 30 seconds or less, in some embodiments about 20 seconds or less, and in some embodiments, from about 0.1 to about 10 seconds. Alternatively, after being placed into contact with an aqueous solution of sodium chloride (0.9 wt. %) for 0.015 kiloseconds ("ks"), the Absorption Rate of the particles may be about 300 g/g/ks or more, in some embodiments about 400 g/g/ks or more, in some embodiments about 500 g/g/ks or more, and in some embodiments, from about 600 to about 1,500 g/g/ks. High Absorption Rates may even be retained for a relatively long period of time. For example, after being placed into contact with an aqueous solution of sodium chloride (0.9 wt. %) for 0.06 ks or even up to 0.12 ks, the Absorption Rate of the particles may still be about 160 g/g/ks or more, in some embodiments about 180 g/g/ks or more, in some embodiments about 200 g/g/ks or more, and in some embodiments, from about 250 to about 1,200 g/g/ks.

Notably, the increased rate of absorption can be maintained without sacrificing the total absorbent capacity of the particles. For example, after 3.6 ks, the total Absorbent Capacity of the particles may be about 10 g/g or more, in some embodiments about 15 g/g or more, and in some embodiments, from about 20 to about 100 g/g. Likewise, the particles may exhibit a Centrifuge Retention Capacity ("CRC") of about 20 grams liquid per gram of superabsorbent particles (g/g) or more, in some embodiments about 25 g/g or more, and in some embodiments, from about 30 to about 60 g/g. Finally, the superabsorbent particles may also exhibit a free swell gel bed permeability ("GBP") of about 40 darcies or less, in some embodiments about 25 darcies or less, and in some embodiments, from about 0.1 to about 10 darcies.

The superabsorbent particles are generally formed from a three-dimensional crosslinked polymer network that contains repeating units derived from one or more ethylenically (e.g., monoethylenically) unsaturated monomeric compounds having at least one hydrophilic radical, such as a carboxyl, carboxylic acid anhydride, carboxylic acid salt, sulfonic acid, sulfonic acid salt, hydroxyl, ether, amide, amino, or quaternary ammonium salt group. Particular examples of suitable ethylenically unsaturated monomeric compounds for forming the superabsorbent particles include, for instance, carboxylic acids (e.g., (meth)acrylic acid (encompasses acrylic acid and/or methacrylic acid), maleic acid, fumaric acid, crotonic acid, sorbic acid, itaconic acid, cinnamic acid, etc.); carboxylic acid anhydrides (e.g., maleic anhydride); salts (alkali metal salts, ammonium salts, amine salts, etc.) of carboxylic acids (e.g., sodium (meth) acrylate, trimethylamine(meth)acrylate, triethanolamine-(meth)acrylate, sodium maleate, methylamine maleate, etc.); vinyl sulfonic acids (e.g., vinylsulfonic acid, allyl sulfonic acid, vinyltoluenesulfonic acid, styrene sulfonic acid, etc.); (meth)acrylic sulfonic acids (e.g., sulfopropyl (meth)acrylate, 2-hydroxy-3-(meth)acryloxy propyl sulfonic acid, etc.); salts of vinyl sulfonic acids or (meth)acrylic sulfonic acids; alcohols (e.g., (meth)allyl alcohol); ethers or esters of polyols (e.g., hydroxyethyl (meth)acrylate, hydroxypropyl (meth)acrylate, triethylene glycol (meth)acrylate, poly(oxyethylene oxypropylene) glycol mono (meth)allyl ether (in which hydroxyl groups may be etherified or esterified), etc.); vinylformamides; (meth)acrylamides, N-alkyl (meth)acrylamides (e.g., N-methylacrylamide, N-hexylacrylamide, etc.), N,N-dialkyl (meth)acrylamides (e.g., N,N-dimethylacrylamide, N,N-di-n-propylacrylamide, etc.); N-hydroxyalkyl (meth)acrylamides (e.g., N-methylol(meth)acrylamide, N-hydroxyethyl-(meth)acrylamide, etc.); N,N-dihydroxyalkyl (meth)acrylamides (e.g., N,N-dihydroxyethyl(meth)acrylamide); vinyl lactams (e.g., N-vinylpyrrolidone); amino group-containing esters (e.g. dialkylaminoalkyl esters, dihydroxyalkylaminoalkyl esters, morpholinoalkyl esters, etc.) of carboxylic acids (e.g., dimethylaminoethyl (meth)acrylate, diethylaminoethyl (meth) acrylate, morpholinoethyl (meth)acrylate, dimethylaminoethyl fumarate, etc.); heterocyclic vinyl compounds (e.g., 2-vinyl pyridine, 4-vinyl pyridine, N-vinyl pyridine, N-vinyl imidazole), etc.); quaternary ammonium salt group-containing monomers (e.g., N,N,N-trimethyl-N-(meth)acryloyloxyethylammonium chloride, N,N,N-triethyl-N-(meth)acryloyloxyethylammonium chloride, 2-hydroxy-3-(meth) acryloyloxypropyl trimethyl ammonium chloride, etc.); and so forth, as well as combinations of any of the foregoing. In most embodiments, (meth)acrylic acid monomeric compounds, as well as salts thereof, are employed to form the superabsorbent particles.

The monomeric compounds referenced above are generally soluble in water. It should be understood, however, that compounds may also be employed that can become water-soluble through hydrolysis. Suitable hydrolyzable monomers may include, for instance, ethylenically unsaturated compounds having at least one hydrolyzable radical, such as esters, amide and nitrile groups. Particular examples of such hydrolysable monomers include methyl (meth)acrylate, ethyl (meth)acrylate, 2-ethylhexyl (meth)acrylate, vinyl acetate, (meth)allyl acetate, (meth)acrylonitrile, etc. Furthermore, it should be understood that additional monomers may be employed so that the resulting particles are formed as a copolymer, such as a random, grafted, or block copolymer. If desired, the comonomer(s) may be selected from the group of monomers listed above. For instance, the comonomer(s) may be (meth)acrylic acid, salt of (meth)acrylic acid, maleic acid anhydride, etc. In one particular embodiment, for example, a copolymer may be formed from acrylic acid (or a salt thereof) and maleic anhydride. In other embodiments, as described in more detail below, a comonomer may also be employed that contains a crosslinkable functionality, such as an alkoxysilane. Regardless of the comonomer(s) employed, it is generally desired that the primary ethylenically unsaturated monomer(s) constitute at least about 50 mol. %, in some embodiments from about 55 mol. % to about 99 mol. %, and in some embodiments, from about 60 mol. % to about 98 mol. % of the monomers used to form the polymer, while comonomer(s) constitute no more than about 60 mol. %, in some embodiments from about 1 mol. % to about 50 mol. %, and in some embodiments, from about 2 mol. % to about 40 mol. % of the monomers used to form the polymer.

To form a network capable of absorbing water, it is generally desired that the polymer is crosslinked during and/or after polymerization. In one embodiment, for instance, the ethylenically unsaturated monomeric compound(s) may be polymerized in the presence of a crosslinking agent to provide a crosslinked polymer. Suitable crosslinking agents typically possess two or more groups that are capable of reacting with the ethylenically unsaturated monomeric compound and that are at least partially water soluble or water dispersible, or at least partially soluble or dispersible in an aqueous monomer mixture. Examples of suitable crosslinking agents may include, for instance, tetraallyloxyethane, N,N'-methylene bisacrylamide, N,N'-methylene bismethacrylamide, triallylamine, trimethylol propane triacrylate, glycerol propoxy triacrylate, divinylbenzene, N-methylol acrylamide, N-methylol methacrylamide, glycidyl methacrylate, polyethylene polyamines, ethyl diamine, ethyl glycol, glycerin, tetraallyloxyethane and triallyl ethers of pentaerythritol, aluminates, silica, alumosilicates, etc., as well as combinations thereof. The amount of the crosslinking agent may vary, but is typically present in an amount of from about 0.005 to about 1.0 mole percent based on moles of the ethylenically unsaturated monomeric compound(s).

In the embodiments described above, crosslinking generally occurs during polymerization. In other embodiments, however, the polymer may contain a latent functionality that is capable of becoming crosslinked when desired. For instance, the polymer may contain an alkoxysilane functionality which, upon exposure to water, forms a silanol functional group that condenses to form a crosslinked polymer. One particular example of such a functionality is a trialkoxysilane having the following general structure:

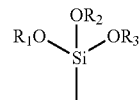

wherein $R_1$, $R_2$ and $R_3$ are alkyl groups independently having from 1 to 6 carbon atoms.

To introduce such a functionality into the polymer structure, a monomeric compound may be employed that contains the functionality, such as an ethylenically unsaturated monomer containing a trialkoxysilane functional group. Particularly suitable monomers are (meth)acrylic acids or salts thereof, such as methacryloxypropyl trimethoxysilane, methacryloxyethyl trimethoxysilane, methacryloxypropyl triethoxysilane, methacryloxypropyl tripropoxysilane, acryloxypropylmethyl dimethoxysilane, 3-acryloxypropyl trimethoxysilane, 3-methacryloxypropylmethyl diethoxysilane, 3-methacryloxypropylmethyl dimethoxysilane, 3-methacryloxypropyl tris(methoxyethoxy)silane, and so forth. In addition to monomers capable of co-polymerization that contain a trialkoxysilane functional group, it is also possible to use a monomer capable of co-polymerization that can subsequently be reacted with a compound containing a trialkoxysilane functional group or a moiety that reacts with water to form a silanol group. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the co-polymer may subsequently be reacted with, for example, but not limited to, tetramethoxysilane.

The superabsorbent polymer particles of the present invention may be prepared by any known polymerization method. For instance, the particles may be prepared by any suitable bulk polymerization technique, such as solution polymerization, inverse suspension polymerization, or emulsion polymerization, such as described in U.S. Pat. Nos. 4,076,663, 4,286,082, 4,340,706, 4,497,930, 4,507,438, 4,654,039, 4,666,975, 4,683,274, or 5,145,906. In solution polymerization, for instance, the monomer(s) are polymerized in an aqueous solution. In inverse suspension polymerization, the monomers(s) are dispersed in an alicyclic or aliphatic hydrocarbon suspension medium in the presence of a dispersing agent, such as a surfactant or protective colloid. If desired, the polymerization reaction may be conducted in the presence of a free radical initiator, redox initiator (reducing and oxidizing agents), thermal initiator, photoinitiator, etc. Examples of suitable reducing agents may include, for instance, ascorbic acid, alkali metal sulfites, alkali metal bisulfites, ammonium sulfite, ammonium bisulfite, alkali metal hydrogen sulfite, ammonium hydrogen sulfite, ferrous metal salts, e.g. ferrous sulfates, sugars, aldehydes, primary and secondary alcohols, etc. Examples of suitable oxidizing agents may include, for instance, hydrogen peroxide, caprylyl peroxide, benzoyl peroxide, cumene peroxide, tertiary butyl diperphthalate, tertiary butyl perbenzoate, sodium percarbonate, sodium peracetate, alkali metal persulfates, ammonium persulfates, alkylhydroperoxides, peresters, diacryl peroxides, silver salts, etc.

If desired, the resulting particles may also be downsized to achieve the desired size noted above. For instance, impact downsizing, which typically employs a grinder having a rotating grinding element, may be used to form the particles. Repeated impact and/or shear stress can be created between the rotating grinding element and a stationary or counter-rotating grinding element. Impact downsizing may also employ air flow to carry and collide the material into a grinding disk (or other shearing element). One particularly suitable impact downsizing apparatus is available commercially from Pallmann Industries (Clifton, N.J.) under the name Turbofiner®, type PLM. In this apparatus, a high activity air whirl is created within a cylindrical grinding chamber between a stationary grinding element and a rotating grinding element of an impact grinding mill. Due to the high air volume, the particles can be impacted and become downsized into the desired particle size. Other suitable impact downsizing processes may be described in U.S. Pat. Nos. 6,431,477 and 7,510,133, both to Pallmann. Another suitable microparticle formation process is cold extrusion downsizing, which generally employs shear and compression forces to form particles having the desired size. For example, the material can be forced through a die at temperatures below the melting point of the matrix polymer. Solid-state shear pulverization is another suitable process that can be used. Such processes generally involve continuous extrusion of the material under high shear and compression conditions while the extruder barrels and a screw are cooled to prevent polymer melting. Examples of such solid state pulverization techniques are described, for instance, in U.S. Pat. No. 5,814,673 to Khait; U.S. Pat. No. 6,479,003 to Furqiuele, et al.; U.S. Pat. No. 6,494,390 to Khait, et al.; U.S. Pat. No. 6,818,173 to Khait; and U.S. Publication No. 2006/0178465 to Torkelson, et al. Yet another suitable microparticle formation technique is known as cryogenic disk milling. Cryogenic disk milling generally employs a liquid (e.g., liquid nitrogen) to cool or freeze the material prior to and/or during grinding. In one embodiment, a single-runner disk milling apparatus can be employed that has a stationary disk and a rotating disk. The material enters between the discs via a channel near the disk center and is formed into particles through the frictional forces created between the discs. One suitable cryogenic disk milling apparatus is available under the name Wedco® cryogenic grinding system from ICO Polymers (Allentown, PA).

Although by no means required, additional components may also be combined with the superabsorbent polymer, before, during, or after polymerization. In one embodiment, for instance, high aspect ratio inclusions (e.g., fibers, tubes, platelets, wires, etc.) may be employed to help produce an internal interlocking reinforcing framework that stabilizes the swelling superabsorbent polymer and improves its resiliency. The aspect ratio (average length divided by median width) to may, for instance, range from about 1 to about 50, in some embodiments from about 2 to about 20, and in some embodiments, from about 4 to about 15. Such inclusions may have a median width (e.g., diameter) of from about 1 to about 35 micrometers, in some embodiments from about 2 to about 20 micrometers, in some embodiments from about 3 to about 15 micrometers, and in some embodiments, from about 7 to about 12 micrometers, as well as a volume average length of from about 1 to about 200 micrometers, in some embodiments from about 2 to about 150 micrometers, in some embodiments from about 5 to about 100 micrometers, and in some embodiments, from about 10 to about 50 micrometers. Examples of such high aspect inclusions may include high aspect ratio fibers (also known as "whiskers") that are derived from carbides (e.g., silicon carbide), silicates (e.g., wollastonite), etc.

If desired, a hydrophobic substance may also be combined with the superabsorbent polymer, such as a substance containing a hydrocarbon group, a substance containing a hydrocarbon group having a fluorine atom, a substance having a polysiloxane structure, etc. Examples of such substances as well as superabsorbent particles formed therefrom are described, for instance, in U.S. Pat. No. 8,742,023 to Fujimura, et al., which is incorporated herein in its entirety by reference thereto. For instance, suitable hydrophobic substances may include polyolefin resins, polystyrene resins, waxes, long-chain fatty acid esters, long-chain fatty acids and salts thereof, long-chain aliphatic alcohols, long-chain aliphatic amides, etc., as well as mixtures thereof. In one particular embodiment, a long-chain fatty acid ester may be employed that is an ester of a fatty acid having 8 to 30 carbon atoms and an alcohol having 1 to 12 carbon atoms, such as methyl laurate, ethyl laurate, methyl stearate, ethyl stearate, methyl oleate, ethyl oleate, glycerol monolaurate, glycerol monostearate, glycerol monooleate, pentaerythritol monolaurate, pentaerythritol monostearate, pentaerythritol monooleate, sorbitol monolaurate, sorbitol monostearate, sorbitol monooleate, sucrose monopalmitate, sucrose dipalmitate, sucrose tripalmitate, sucrose monostearate, sucrose distearate, sucrose tristearate, tallow, etc. In another embodiment, a long-chain fatty acid or a salt thereof may be employed that contains 8 to 30 carbon atoms, such as lauric acid, palmitic acid, stearic acid, oleic acid, dimer acid, behenic acid, etc., as well as zinc, calcium, magnesium, and/or aluminum salts thereof, such as calcium palmitate, aluminum palmitate, calcium stearate, magnesium stearate, aluminum stearate, etc.

Regardless of the specific manner in which the particles are formed, a variety of different techniques can be employed to initiate the creation of the desired porous network. In certain embodiments, control over the polymerization process itself can lead to the formation of pores within the resulting particles. For instance, polymerization may be conducted in heterogeneous, two phase or multiphase systems, with a monomer-rich continuous phase suspended in a solvent-rich minority phase. As the monomer-rich phase begins to polymerize, pore formation can be induced by the solvent-rich phase. Of course, techniques may also be employed in which a porous network is formed within preformed particles. In one particular embodiment, for instance, a technique known as "phase inversion" may be employed in which a polymer dissolved or swollen in a continuous phase solvent system inverts into a continuous phase solid macromolecular network formed by the polymer. This inversion can be induced through several methods, such as by removal of the solvent via a dry process (e.g., evaporation or sublimation), addition of a non-solvent or addition to a non-solvent via a wet process. In dry processes, for example, the temperature (or the pressure) of the particles can be altered so that the solvent system (e.g., water) can be transformed to another state of matter that can be removed without excessive shrinkage, either by evacuating or purging with a gas. Freeze drying, for instance, involves cooling the solvent system below its freezing point and then allowing it to sublime under reduced pressure so that pores are formed. Supercritical drying, on the other hand, involves heating the solvent system under pressure above the supercritical point so that pores are formed.

Wet processes, however, are particularly suitable in that they do not rely on a substantial degree of energy to achieve the desired inversion. In a wet process, the superabsorbent polymer and solvent system may be provided in the form of a single phase homogenous composition. The concentration of the polymer typically ranges from about 0.1% to about 20% wt./vol., and in some embodiments, from about 0.5% to about 10% wt./vol. of the composition. The composition is thereafter contacted with a non-solvent system using any known technique, such as by immersing into a bath, countercurrent washing, spray washing, belt spray, and filtering. The difference in chemical potential between the solvent and non-solvent systems causes molecules of the solvent to diffuse out of the superabsorbent polymer, while molecules of the non-solvent diffuse into the polymer. Ultimately, this causes the polymer composition to undergo a transition from a single phase homogeneous composition to an unstable two phase mixture containing polymer-rich and polymer-poor fractions. Micellar droplets of the non-solvent system in the polymer-rich phase also serve as nucleation sites and become coated with polymer, and at a certain point, these droplets precipitate to form a continuous polymer network. The solvent composition inside the polymer matrix also collapses on itself and forms voids. The matrix can then be dried to remove the solvent and non-solvent systems and form stabile porous particles.

The exact solvent and non-solvent systems employed to accomplish the phase inversion are not particularly critical, so long they are selected in tandem based on their miscibility. More particularly, the solvent and non-solvent systems can be selected so that they have a specific difference in their Hildebrand solubility parameters, $\delta$, which is a predictive indicator of the miscibility of two liquids with higher values generally representing a more hydrophilic liquid and lower values representing a more hydrophobic liquid. It is generally desired that the difference in the Hildebrand solubility parameter of the solvent system and the non-solvent system (e.g., $\delta_{solvent}$-$\delta_{non-solvent}$) is from about 1 to about 15 calories$^{1/2}$/cm$^{3/2}$, in some embodiments from about 4 to about 12 calories$^{1/2}$/cm$^{3/2}$, and in some embodiments, from about 6 to about 10 calories$^{1/2}$/cm$^{3/2}$. Within these ranges, the solvent/non-solvent will have enough miscibility to allow solvent extraction to occur, but not too miscible so that phase inversion could not be accomplished. Suitable solvents for use in the solvent system may include, for instance, water, aqueous alcohol, saline, glycerol, etc., as well as combinations thereof. Likewise, suitable non-solvents for use in the non-solvent system may include acetone, n-propyl alcohol, ethyl alcohol, methanol, n-butyl alcohol, propylene glycol, ethylene glycol, etc., as well as combinations thereof.

Typically, the volume ratio of the solvent system to the non-solvent system ranges from about 50:1 to about 1:200 (volume per volume), in some embodiments from about 10:1 to about 1:180 (volume per volume), in some embodiments from about 1:1 to about 1:160 (volume per volume), in some embodiments from about 1:60 to about 1:150 (volume per volume), in some embodiments from about 1:1 to about 1:60 (volume per volume), and in some embodiments from about 1:1 to about 1:2 (volume per volume). After contact with the non-solvent and the phase inversion is completed, the liquid phase may be dried and/or removed using any suitable technique, such as by increased temperature, time, vacuum, and/or flow rate control using any suitable equipment (e.g., forced air ovens and vacuum ovens). In one example, for instance, high temperature drying at temperatures up to about 175° C. can leave up to about 16% wt. ethanol in the sample. The sample can then be placed in a humidity chamber at 69° C. at a 50% relative humidity to reduce the ethanol content to less than 0.13%.

The present invention may be better understood with reference to the following examples.

Test Methods

Pore Properties

The pore properties (e.g., average pore diameter, total pore area, bulk density, pore size distribution, and percent porosity) of superabsorbent particles may be determined using mercury porosimetry (also known as mercury intrusion) as is well known in the art. For example, a commercially available porosimeter, such as AutoPore IV 9500 from Micrometrics, may be employed. Such devices generally characterize porosity by applying various levels of pressure to a sample immersed in mercury. The pressure required to intrude mercury into the sample's pores is inversely proportional to the size of the pores. Measurements may be performed at an initial pressure of 0.58 psi and at a final pressure of about 60,000 psi. The average pore diameter, total pore area, and bulk density may be directly measured during the mercury intrusion test. The overall pore size distribution may be derived from a graph of differential intrusion and pore diameter (μm). Likewise, the percent porosity may be calculated based on the reduction in bulk density reduction (assuming a constant size, packing, and shape of the particles) taking into consideration that approximately 50% of volume is occupied by empty space due to particles packing. More particularly, the percent porosity may be determined according to the following equation:

$$100 \times 0.5 \times [(\text{Bulk Density of Control Sample} - \text{Bulk Density of Test Sample})/\text{Bulk Density of Control Sample}]$$

wherein the Bulk Density (g/cm$^3$) is determined by mercury intrusion at a pressure of 0.58 psi.

Absorbent Capacity

The absorbent capacity of superabsorbent particles can be measured using an Absorbency Under Load ("AUL") test, which is a well-known test for measuring the ability of superabsorbent particles to absorb a 0.9 wt. % solution of sodium chloride in distilled water at room temperature (test solution) while the material is under a load. For example, 0.16 grams of superabsorbent particles may be confined within a 5.07 cm$^2$ area of an Absorbency Under Load ("AUL") cylinder under a nominal pressure of 0.01 psi, 0.3 psi, or 0.9 psi. The sample is allowed to absorb the test solution from a dish containing excess fluid. At predetermined time intervals, a sample is weighed after a vacuum apparatus has removed any excess interstitial fluid within the cylinder. This weight versus time data is then used to determine the Absorption Rates at various time intervals.

Figure 2:
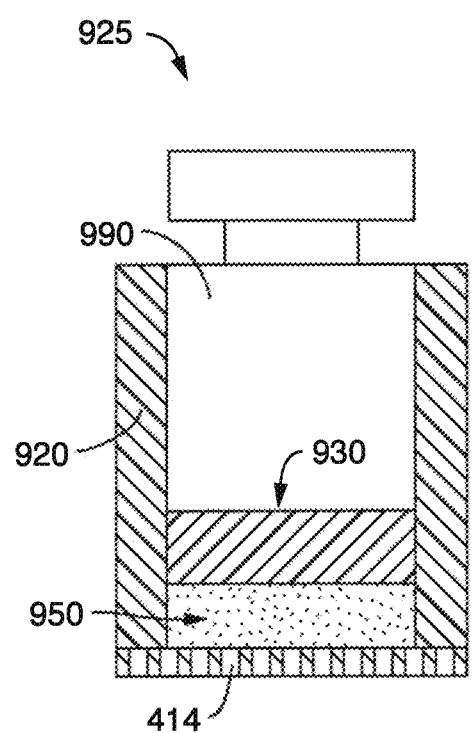
FIG. 2 shows the AUL assembly FIG. 1.
Figure 3A:
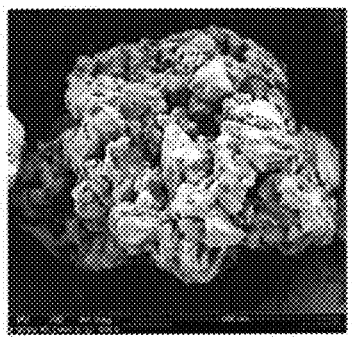
FIG. 3 shows SEM microphotographs of the superabsorbent particles of Example 1, wherein FIG. 3A (456×), FIG. 3B (10,000×, fractured), and FIG. 3C (55,000×, fractured) show the particles prior to pore formation and FIG. 3D (670×), FIG. 3E (10,000×, fractured) and FIG. 3F (55,000×, fractured) show the particles after pore formation.
Figure 3B:
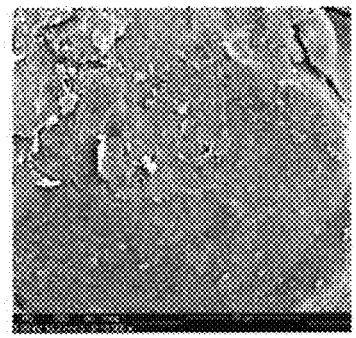
Figure 3C:
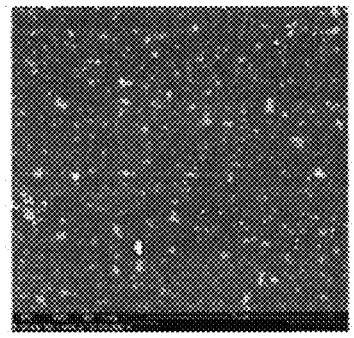
Figure 3D:
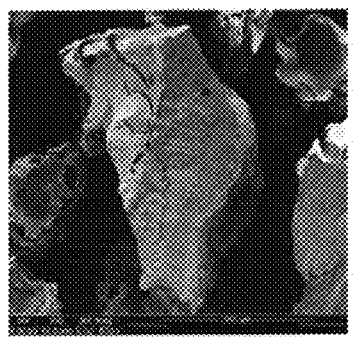
Figure 3E:
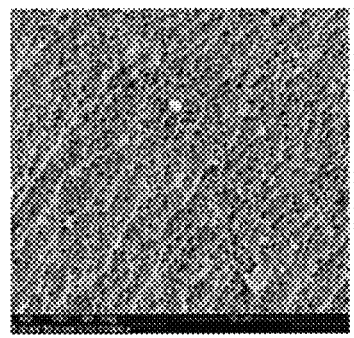
Figure 3F:
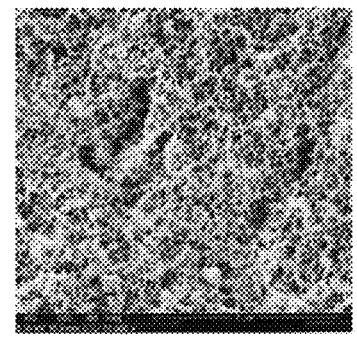
Figure 4:
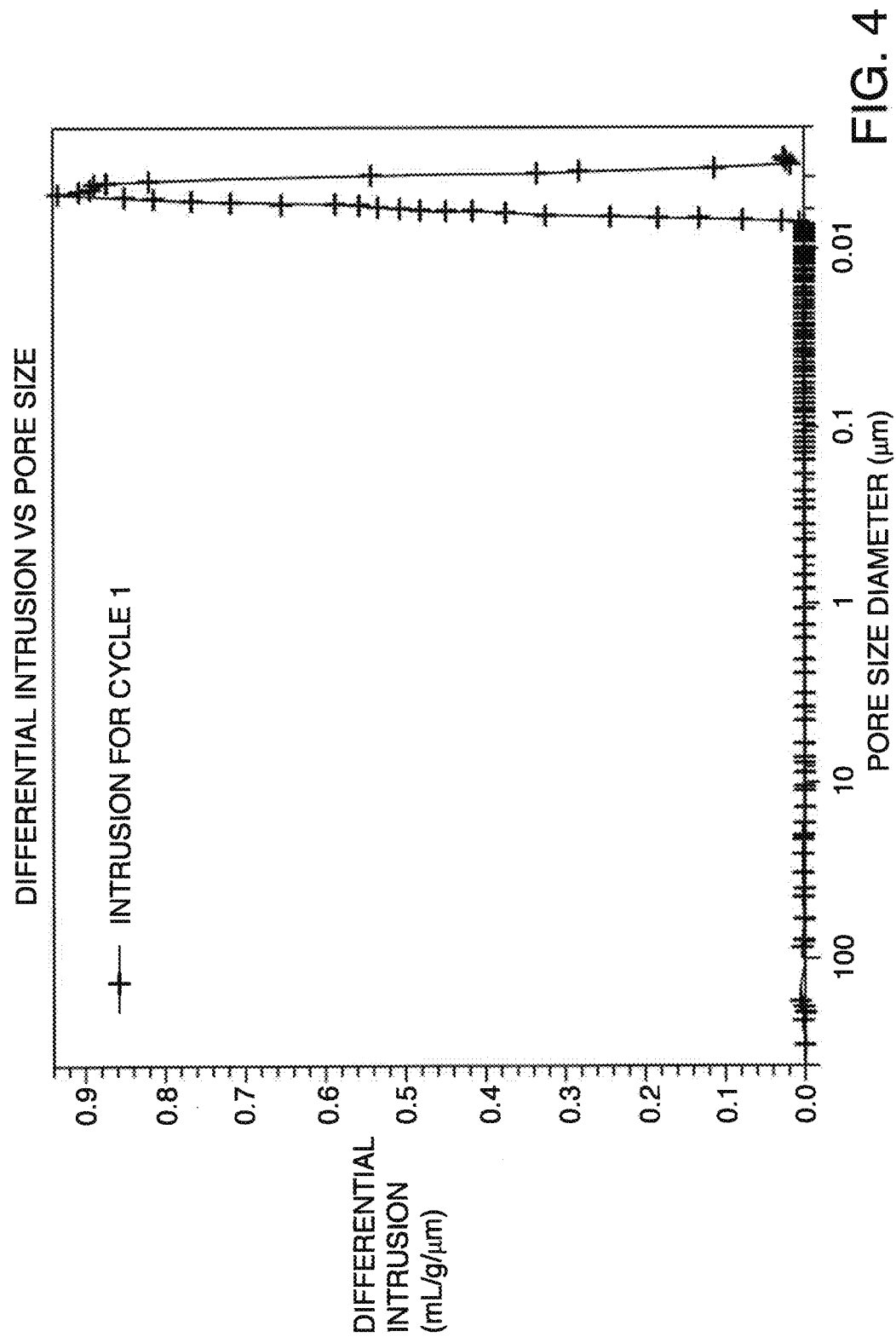
FIG. 4 shows the pore size distribution of the control particles referenced in Example 1 prior to solvent exchange.
Figure 5:
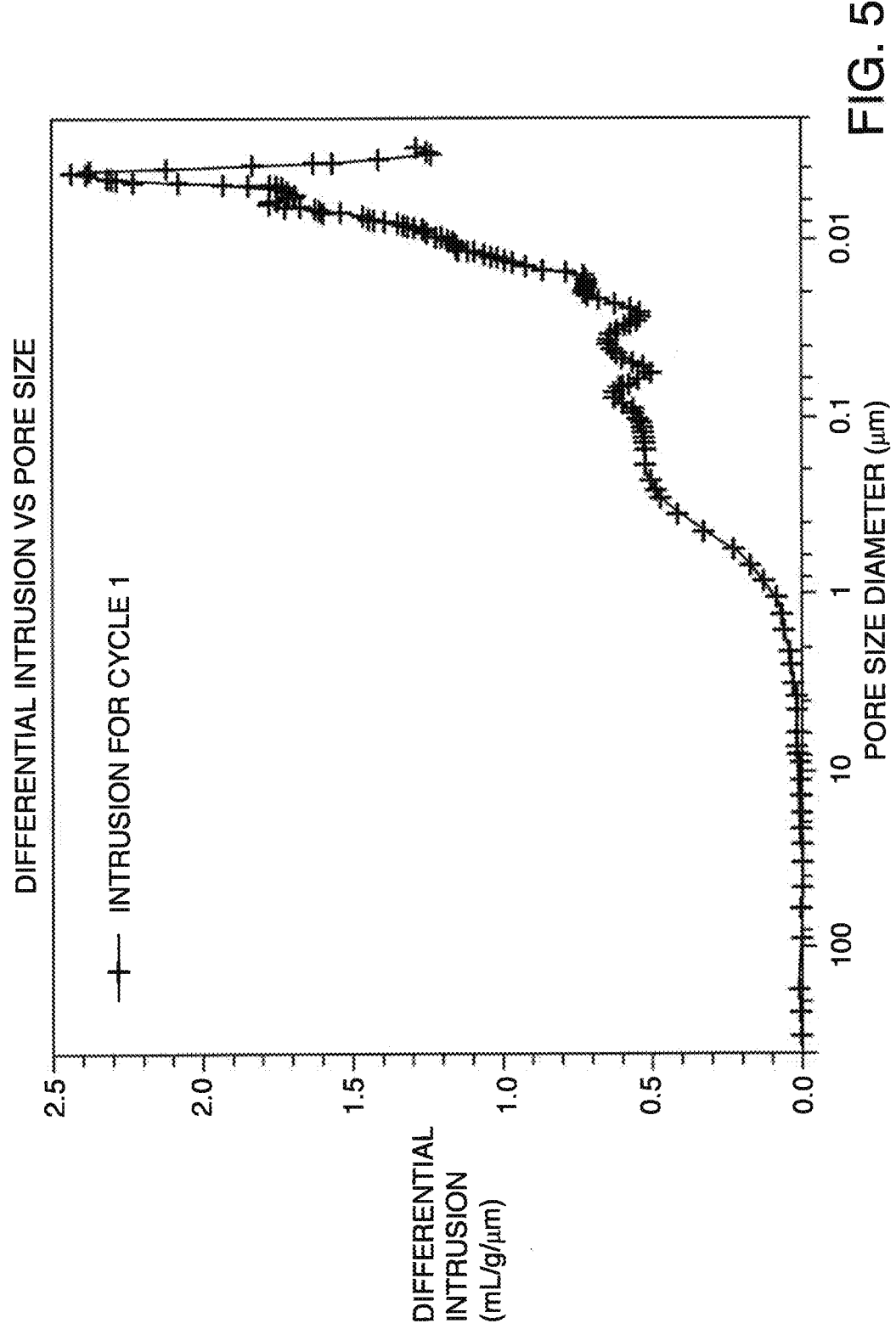
FIG. 5 shows the pore size distribution of the particles of Example 1 after solvent exchange with methanol.
Figure 6:
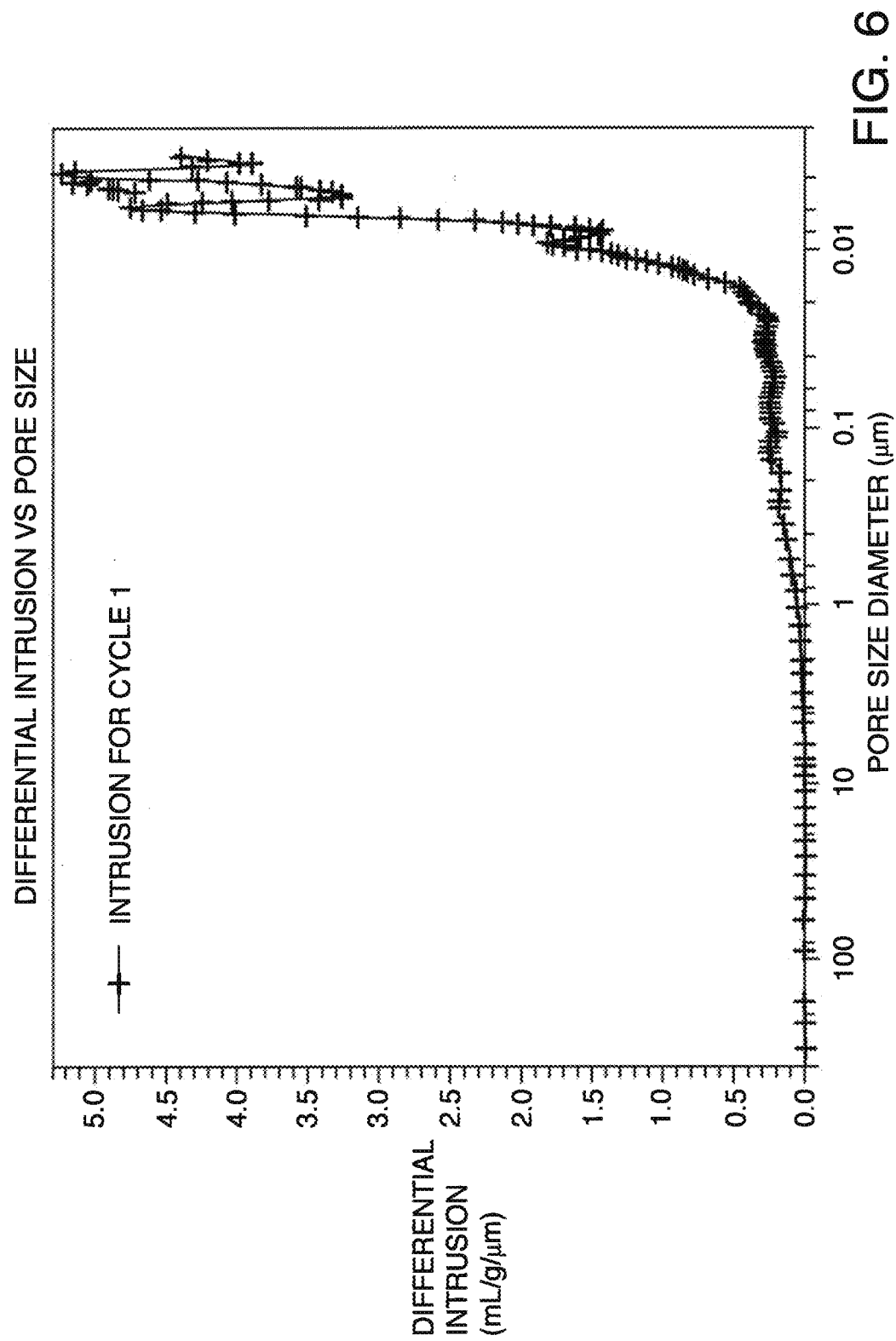
FIG. 6 shows the pore size distribution of the particles of Example 2 after solvent exchange with ethanol.
Figure 7:
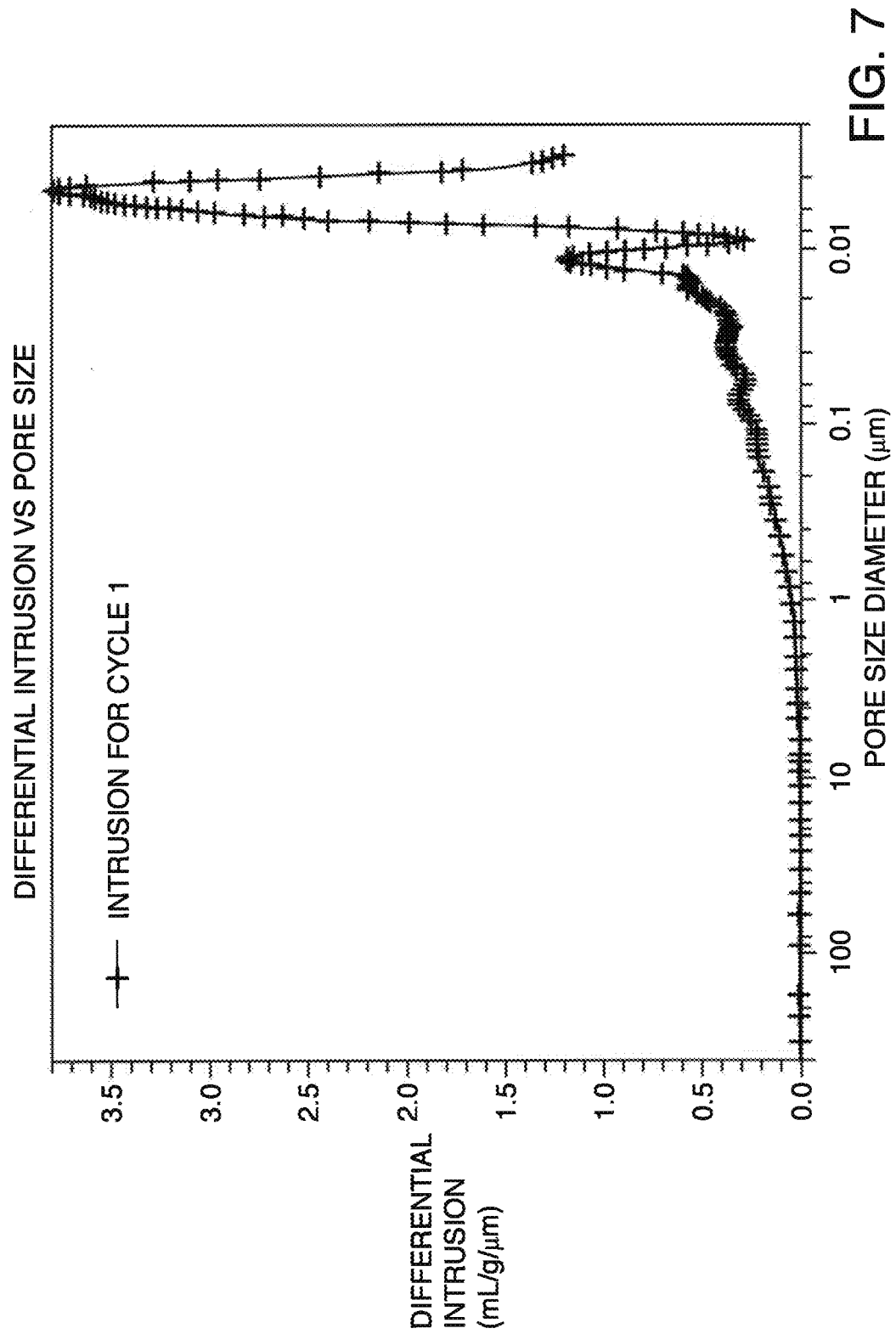
FIG. 7 shows the pore size distribution of the particles of Example 3 after solvent exchange with isopropyl alcohol.
Figure 8:
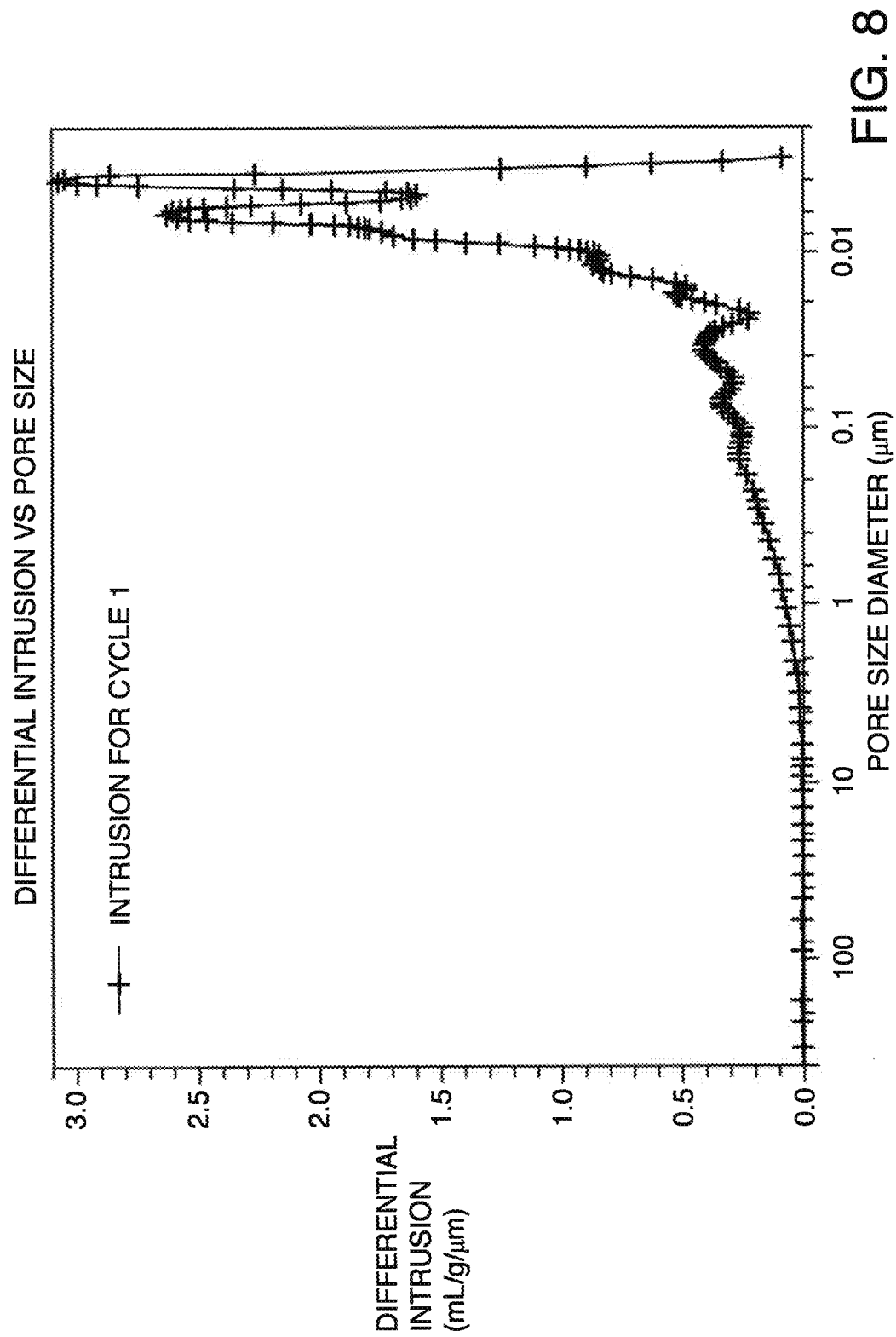
FIG. 8 shows the pore size distribution of the particles of Example 4 after solvent exchange with acetone.

Referring to FIG. 1, for instance, one embodiment of an apparatus 910 that can be used to determine absorbent capacity is shown. The apparatus 910 includes an AUL assembly 925 having a cylinder 920, a piston 930 and weight 990. The weight 990 may be a 100-gram weight. A side arm flask 960 may be employed that is fitted with a rubber stopper 945 and tube 955 in the top of the flask to help trap any fluid removed from the sample before it enters the vacuum system. Rubber or plastic tubing 970 may be used to the side arm flask 960 and an AUL chamber 940. Additional tubing 970 may also be used to connect a vacuum source (not shown) and a side arm 980 of the flask 960. Referring to FIG. 2, the cylinder 920 may be used to contain superabsorbent particles 950 and may be made from one-inch (2.54 cm) inside diameter acrylic tubing machined-out slightly to be sure of concentricity. After machining, a mesh cloth 414 (e.g., 400 mesh) may be attached to the bottom of the cylinder 920 using an appropriate solvent that causes the screen to be securely adhered to the cylinder. The piston 930 may be a 4.4-g piston made from 1-inch (2.5 cm) diameter solid material (e.g., acrylic) and may be machined to closely fit without binding in the cylinder 920. As noted above, the apparatus 910 also includes an AUL chamber 940 that removes interstitial liquid picked up during the swelling of the superabsorbent particles 950. This test apparatus is similar to a GATS (gravimetric absorbency test system), available from M/K Systems, as well as the system described by Lichstein at pages 129-142 of the INDA Technological Symposium Proceedings, March 1974. A ported disk 935 is also utilized having ports confined within a 2.5-centimeter diameter area.

To carry out the test, the following steps may be performed:

(1) Wipe the inside of the AUL cylinder 920 with an anti-static cloth, and weigh the cylinder 920, weight 990 and piston 930;

(2) Record the weight as CONTAINER WEIGHT in grams to the nearest milligram;

(3) Slowly pour the 0.16±0.005 gram sample of the superabsorbent particles 950 into the cylinder 920 so that the particles do not make contact with the sides of the cylinder or it may adhere to the walls of the AUL cylinder;

(4) Weigh the cylinder 920, weight 990, piston 930, and superabsorbent particles 950 and record the value on the balance, as DRY WEIGHT in grams to the nearest milligram;

(5) Gently tap the AUL cylinder 920 until the superabsorbent particles 950 are evenly distributed on the bottom of the cylinder;

(6) Gently place the piston 930 and weight 990 into the cylinder 920;

(7) Place the test fluid (0.9 wt. % aqueous sodium chloride solution) in a fluid bath with a large mesh screen on the bottom;

(8) Simultaneously start the timer and place the superabsorbent particles 950 and cylinder assembly 925 onto the screen in the fluid bath. The level in the bath should be at a height to provide at least a 1 cm positive head above the base of the cylinder;

(9) Gently swirl the sample to release any trapped air and ensure the superabsorbent particles are in contact with the fluid.

(10) Remove the cylinder 920 from the fluid bath at a designated time interval and immediately place the cylinder on the vacuum apparatus (ported disk 935 on the top of the AUL chamber 940) and remove excess interstitial fluid for 10 seconds;

(11) Wipe the exterior of the cylinder with paper toweling or tissue;

(12) Weigh the AUL assembly (i.e., cylinder 920, piston 930 and weight 990), with the superabsorbent particles and any absorbed test fluid immediately and record the weight as WET WEIGHT in grams to the nearest milligram and the time interval; and

(13) Repeat for all time intervals needed.

At least two (2) samples are generally tested at each predetermined time interval. The time intervals are typically 15, 30, 60, 120, 300, 600, 1800 and 3600 seconds (or 0.015, 0.030, 0.060, 0.120, 0.300, 0.600, 1.8, or 3.6 kiloseconds). The "absorbent capacity" of the superabsorbent particles at a designated time interval is calculated in grams liquid by grams superabsorbent by the following formula:

$$(\text{Wet Weight} - \text{Dry Weight})/(\text{Dry Weight} - \text{Container Weight})$$

Absorption Rate

The "Absorption Rate" of superabsorbent particles can be determined at a designated time interval by dividing the Absorbent Capacity (g/g) described above by the specific time interval (kiloseconds, ks) of interest, such as 0.015, 0.030, 0.060, 0.120, 0.300, 0.600, 1.8, or 3.6 kiloseconds.

Centrifuge Retention Capacity (CRC)

The Centrifuge Retention Capacity (CRC) test measures the ability of superabsorbent particles to retain liquid after being saturated and subjected to centrifugation under controlled conditions. The resultant retention capacity is stated as grams of liquid retained per gram weight of the sample (g/g). The sample to be tested is prepared from particles that are prescreened through a U.S. standard 30-mesh screen and retained on a U.S. standard 50-mesh screen. The particles can be prescreened by hand or automatically and are stored in a sealed airtight container until testing. The retention capacity is measured by placing 0.2±0.005 grams of the prescreened sample into a water-permeable bag that will contain the sample while allowing a test solution (0.9 weight percent sodium chloride in distilled water) to be freely absorbed by the sample. A heat-sealable tea bag material, such as model designation 1234T heatsealable filter paper, may be suitable. The bag is formed by folding a 5-inch by 3-inch sample of the bag material in half and heat-sealing two of the open edges to form a 2.5-inch by 3-inch rectangular pouch. The heat seals may be about 0.25 inches inside the edge of the material. After the sample is placed in the pouch, the remaining open edge of the pouch may also be heat-sealed. Empty bags may be made to serve as controls. Three samples (e.g., filled and sealed bags) are prepared for the test. The filled bags are tested within three minutes of preparation unless immediately placed in a sealed container, in which case the filled bags must be tested within thirty minutes of preparation.

The bags are placed between two TEFLON® coated fiberglass screens having 3-inch openings (Taconic Plastics, Inc., Petersburg, N.Y.) and submerged in a pan of the test solution at 23° C., making sure that the screens are held down until the bags are completely wetted. After wetting, the samples remain in the solution for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples may be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the centrifuge retention capacity is determined as:

Sample Bag Weight After Centrifuge–Empty Bag Weight After Centrifuge–Dry Sample Weight/ Dry Sample Weight The three samples are tested and the results are averaged to determine the retention capacity (CRC) of the superabsorbent material. The samples are tested at 23° C. and 50% relative humidity.

Vortex Time

The Vortex Time is the amount of time in seconds required for a predetermined mass of superabsorbent particles to close a vortex created by stirring 50 milliliters of 0.9 percent by weight sodium chloride solution at 600 revolutions per minute on a magnetic stir plate. The time it takes for the vortex to close is an indication of the free swell absorbing rate of the particles. The vortex time test may be performed at a temperature is 23° C. and relative humidity of 50% according to the following procedure:

(1) Measure 50 milliliters (±0.01 milliliter) of 0.9 percent by weight sodium chloride solution into the 100-milliliter beaker.
(2) Place a 7.9 millimeters×32 millimeters TEFLON® covered magnetic stir bar without rings (such as that commercially available under the trade designation SIP® brand single pack round stirring bars with removable pivot ring) into the beaker.
(3) Program a magnetic stir plate (such as that commercially available under the trade designation DATA-PLATE® Model #721) to 600 revolutions per minute.
(4) Place the beaker on the center of the magnetic stir plate such that the magnetic stir bar is activated. The bottom of the vortex should be near the top of the stir bar. The superabsorbent particles are pre-screened through a U.S. standard #30 mesh screen (0.595 millimeter openings) and retained on a U.S. standard #50 mesh screen (0.297 millimeter openings).
(5) Weigh out the required mass of the superabsorbent particles to be tested on weighing paper.
(6) While the sodium chloride solution is being stirred, quickly pour the absorbent polymer to be tested into the saline solution and start a stopwatch. The superabsorbent particles to be tested should be added to the saline solution between the center of the vortex and the side of the beaker.
(7) Stop the stopwatch when the surface of the saline solution becomes flat and record the time. The time, recorded in seconds, is reported as the vortex time.

Free-Swell Gel Bed Permeability (GBP) Test

As used herein, the Free Swell Gel Bed Permeability (GBP) Test determines the permeability of a swollen bed of superabsorbent material under what is commonly referred to as "free swell" conditions. The term "free swell" means that the superabsorbent material is allowed to swell without a swell restraining load upon absorbing test solution as will be described. This test is described in U.S. Patent Publication No. 2010/0261812 to Qin, which is incorporated herein by reference thereto. For instance, a test apparatus may be employed that contains a sample container and a piston, which may include a cylindrical LEXAN shaft having a concentric cylindrical hole bored down the longitudinal axis of the shaft. Both ends of the shaft may be machined to provide upper and lower ends. A weight may rest on one end that has a cylindrical hole bored through at least a portion of its center. A circular piston head may be positioned on the other end and provided with a concentric inner ring of seven holes, each having a diameter of about 0.95 cm, and a concentric outer ring of fourteen holes, each having a diameter of about 0.95 cm. The holes are bored from the top to the bottom of the piston head. The bottom of the piston head may also be covered with a biaxially stretched mesh stainless steel screen. The sample container may contain a cylinder and a 100-mesh stainless steel cloth screen that is biaxially stretched to tautness and attached to the lower end of the cylinder. Superabsorbent particles can be supported on the screen within the cylinder during testing.

The cylinder may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 5 cm. Drainage holes may be formed in the sidewall of the cylinder at a height of approximately 4.0 cm above the screen to allow liquid to drain from the cylinder to thereby maintain a fluid level in the sample container at approximately 4.0 cm above the screen. The piston head may be machined from a LEXAN rod or equivalent material and has a height of approximately 16 mm and a diameter sized such that it fits within the cylinder with minimum wall clearance but still slides freely. The shaft may be machined from a LEXAN rod or equivalent material and has an outer diameter of about 2.22 cm and an inner diameter of about 0.64 cm. The shaft upper end is approximately 2.54 cm long and approximately 1.58 cm in diameter, forming an annular shoulder to support the annular weight. The annular weight, in turn, has an inner diameter of about 1.59 cm so that it slips onto the upper end of the shaft and rests on the annular shoulder formed thereon. The annular weight can be made from stainless steel or from other suitable materials resistant to corrosion in the presence of the test solution, which is 0.9 wt. % sodium chloride solution in distilled water. The combined weight of the piston and annular weight equals approximately 596 grams, which corresponds to a pressure applied to the sample of about 0.3 pounds per square inch, or about 20.7 dynes/cm$^2$, over a sample area of about 28.27 cm$^2$. When the test solution flows through the test apparatus during testing as described below, the sample container generally rests on a 16-mesh rigid stainless steel support screen. Alternatively, the sample container may rest on a support ring diametrically sized substantially the same as the cylinder so that the support ring does not restrict flow from the bottom of the container.

To conduct the Gel Bed Permeability Test under "free swell" conditions, the piston, with the weight seated thereon, is placed in an empty sample container and the height from the bottom of the weight to the top of the cylinder is measured using a caliper or suitable gauge accurate to 0.01 mm. The height of each sample container may be measured empty and which piston and weight is used may be tracked when using multiple test apparatus. The same piston and weight may be used for measurement when the sample is later swollen following saturation. The sample to be tested is prepared from superabsorbent particles that are pre-screened through a U.S. standard 30-mesh screen and retained on a U.S. standard 50-mesh screen. The particles can be prescreened by hand or automatically. Approximately 0.9 grams of the sample is placed in the sample container, and the container, without the piston and weight therein, is then submerged in the test solution for a time period of about 60 minutes to saturate the sample and allow the sample to swell free of any restraining load. At the end of this period, the piston and weight assembly is placed on the saturated sample in the sample container and then the sample container, piston, weight, and sample are removed from the solution. The thickness of the saturated sample is determined by again measuring the height from the bottom of the weight to the top of the cylinder, using the same caliper or gauge used previously provided that the zero point is unchanged from the initial height measurement. The height measurement obtained from measuring the empty sample container, piston, and weight is subtracted from the height measurement obtained after saturating the sample. The resulting value is the thickness, or height "H" of the swollen sample.

The permeability measurement is initiated by delivering a flow of the test solution into the sample container with the saturated sample, piston, and weight inside. The flow rate of test solution into the container is adjusted to maintain a fluid height of about 4.0 cm above the bottom of the sample container. The quantity of solution passing through the sample versus time is measured gravimetrically. Data points are collected every second for at least twenty seconds once the fluid level has been stabilized to and maintained at about 4.0 cm in height. The flow rate Q through the swollen sample is determined in units of grams/second (g/s) by a linear least-square fit of fluid passing through the sample (in grams) versus time (in seconds). The permeability is obtained by the following equation:

$$K=(1.01325\times10^8)*[Q*H*Mu]/[A*Rho*P]$$

where
K=Permeability (darcies),
Q=flow rate (g/sec),
H=height of sample (cm),
Mu=liquid viscosity (poise) (approximately 1 centipoise for the test solution used with this test),
A=cross-sectional area for liquid flow (cm$^2$),
Rho=liquid density (g/cm$^3$) (approximately 1 g/cm$^3$ for the test solution used with this Test), and
P=hydrostatic pressure (dynes/cm$^2$) (normally approximately 3,923 dynes/cm$^2$), which may be calculated from Rho*g*h, where Rho=liquid density (g/cm$^3$), g=gravitational acceleration, nominally 981 cm/sec$^2$, and h=fluid height, e.g., 4.0 cm.

A minimum of three samples is tested and the results are averaged to determine the free swell gel bed permeability of the sample. The samples are tested at 23° C. and 50% relative humidity.

Example 1

15.00 grams of commercially available crosslinked polyacrylate superabsorbent particles were initially provided. The particles were formed in a manner as described in U.S. Pat. No. 8,742,023 to Fuiimura, et al. and had an initial Vortex Time of 35 seconds and CRC of about 27.5 g/g. The particles were swollen in excess of a good solvent (i.e., saline) for 60 minutes to reach equilibrium swelling capacity. Next, excess of saline was drained and interstitial liquid removed using a vacuum filtration technique. The vacuum filtration system was comprised of a Buchner funnel, moistened filter paper, Buchner flask, rubber bung and vacuum tubing. The swollen superabsorbent particles were then manually transferred into 1 kg of high purity ACS grade methanol under constant stirring in 2 L Pyrex beaker. Stirring was performed with a magnetic bar with dimensions: L=5 cm, D=0.9 cm and a rate of stirring of 800-1000 rpm. After 30 minutes, the solvent mixture was drained and another 1 kg of fresh methanol was added to superabsorbent particles. After 30 minutes, the solvent mixture was again drained and the superabsorbent particles were transferred to a Teflon Petri dish and dried for 1 hour in air forced oven at 85° C. Then, the superabsorbent particles were transferred into a vacuum oven to complete drying and remove residual methanol. Drying occurred at a temperature of 120-140° C. and pressure of 30 in Hg for 4 hours. The dried superabsorbent particles were then adjusted using set of sieves with mesh size of 45-850 microns. Particles with a size of 300-600 microns in diameter were collected for further evaluation.

Example 2

Particles were formed as described in Example 1, except that ACS grade 200 proof high purity ethanol was used during the solvent/non-solvent exchange step.

Example 3

Particles were formed as described in Example 1, except that isopropyl alcohol was used during the solvent/non-solvent exchange step.

Example 4

Particles were formed as described in Example 1, except that acetone was used during the solvent/non-solvent exchange step.

Various pore properties were also determined for Examples 1-4 using the test referend above. The pore size distribution for the samples is shown in FIGS. 4-8 and the results are set forth in the table below.

| Example | Average Pore Diameter (nm) | Total Pore Area, (m$^2$/g) | Bulk Density at 0.58 PSI, (g/cm$^3$) | Pore Size Range, (nm) | Porosity, (%) |
|---|---|---|---|---|---|
| 1 | 534 | 18.5 | 0.3085 | 10-1,000 | 28 |
| 2 | 306 | 22.1 | 0.3983 | 10-1,000 | 22 |
| 3 | 331 | 16.4 | 0.5538 | 10-1,000 | 11 |
| 4 | 407 | 15.2 | 0.4356 | 10-4,000 | 19 |
| Control (prior to solvent exchange) | 1,810 | 1.7 | 0.7003 | <10 | — |

Example 5

Particles were formed as described in Example 2 except that the particles were initially swollen in a 5 wt. % solution of sodium chloride.

Example 6

Particles were formed as described in Example 2 except that the particles were initially swollen in a 10 wt. % solution of sodium chloride.

Example 7

Particles were formed as described in Example 2 except that the particles were initially swollen in a 15 wt. % solution of sodium chloride.

Example 8

Particles were formed as described in Example 2 except that the particles were initially swollen in a 20 wt. % solution of sodium chloride.

Example 9

Particles were formed as described in Example 2 except that the particles were initially swollen in a 30 wt. % solution of ACS grade 200 proof high purity ethanol in di-ionized water.

Example 10

Particles were formed as described in Example 2 except that the particles were initially swollen in a 40 wt. % solution of ACS grade 200 proof high purity ethanol in di-ionized water.

Example 11

Particles were formed as described in Example 2 except that the particles were initially swollen in a 50 wt. % solution of ACS grade 200 proof high purity ethanol in di-ionized water.

Example 12

Particles were formed as described in Example 2 except that the particles were initially swollen in a 60 wt. % solution of ACS grade 200 proof high purity ethanol in di-ionized water.

Example 13

Particles were formed as described in Example 2 except that the particles were initially swollen in a 80 wt. % solution of ACS grade 200 proof high purity ethanol in di-ionized water.

Example 14

Particles were formed as described in Example 1, except that the time of solvent/non-solvent exchange was reduced from 30 min to 15 min per step.

Example 15

Particles were formed as described in Example 1, except that the time of solvent/non-solvent exchange was reduced from 30 min to 5 min per step.

Example 16

Particles were formed as described in Example 1, except that the amount of methanol was reduced from 1 kg to 0.5 kg per step.

Example 17

Particles were formed as described in Example 16, except that the time of solvent/poor solvent exchange was reduced from 30 minutes to 15 minutes.

Example 18

Particles were formed as described in Example 16, except that the time of solvent/poor solvent exchange was reduced from 30 minutes to 5 minutes.

Example 19

15.00 grams of the same superabsorbent particles provided in Example 1 were manually transferred into 1 kg of high purity ACS grade methanol under constant stirring in 2 L Pyrex beaker. Stirring was performed with a magnetic bar with dimensions: L=5 cm, D=0.9 cm and a rate of stirring of 800-1000 rpm. After 30 minutes, the solvent mixture was drained and another 1 kg of fresh methanol was added to superabsorbent particles. After 30 minutes, the solvent mixture was again drained and the superabsorbent particles were transferred to a Teflon Petri dish and dried for 1 hour in air forced oven at 85° C. Then, the superabsorbent particles were transferred into a vacuum oven to complete drying and remove residual methanol. Drying occurred at a temperature of 120-140° C. and pressure of 30 inHg for 4 hours. The dried superabsorbent particles were then adjusted using set of sieves with mesh size of 45-850 microns. Particles with a size of 300-600 microns in diameter were collected for further evaluation.

Example 20

Particles were formed as described in Example 19, except that high purity ethanol was used to wash the superabsorbent particles.

Example 21

Particles were formed as described in Example 19, except that high purity isopropyl alcohol was used to wash the superabsorbent particles.

Example 22

Particles were formed as described in Example 19, except that high purity acetone was used to wash the superabsorbent particles.

The samples of Examples 1-22 were tested for vortex time and CRC as discussed above.
The results are set forth below.

| Example | Vortex Time (s) | CRC (g/g) |
| --- | --- | --- |
| 1 | 8 | 29.9 |
| 2 | 11 | 28.1 |
| 3 | 13 | 30.0 |
| 4 | 18 | 29.6 |
| 5 | 14 | 27.4 |
| 6 | 34 | 18.2 |
| 7 | 55 | 15.7 |
| 8 | 83 | 13.5 |
| 9 | 13 | 30.0 |
| 10 | 15 | 30.5 |
| 11 | 18 | 30.8 |
| 12 | 18 | 31.7 |
| 13 | 32 | 30.9 |
| 14 | 9 | 27.3 |
| 15 | 9 | 28.9 |
| 16 | 22 | 30.3 |
| 17 | 21 | 29.6 |
| 18 | 30 | 30.7 |
| 19 | 35 | 20.3 |

-continued

| Example | Vortex Time (s) | CRC (g/g) |
|---|---|---|
| 20 | 35 | 29.3 |
| 21 | 36 | 30.3 |
| 22 | 37 | 28.0 |

The superabsorbent particles of Example 1 were also tested for AUL (at 0.01 psi) before and after being subjected to the solvent exchange procedure. The resulting properties are set forth below.

| | Prior to Solvent Exchange | | After Solvent Exchange | |
|---|---|---|---|---|
| Time (ks) | Absorbent Capacity (g/g) | Absorption Rate (g/g/ks) | Absorbent Capacity (g/g) | Absorption Rate (g/g/ks) |
| 0.015 | 3.86 | 257 | 11.35 | 757 |
| 0.030 | 7.23 | 241 | 15.29 | 510 |
| 0.060 | 13.56 | 226 | 19.47 | 325 |
| 0.120 | 19.12 | 159 | 23.76 | 198 |
| 0.300 | 23.89 | 80 | 27.15 | 91 |
| 0.600 | 26.68 | 45 | 28.64 | 48 |
| 1.800 | 29.14 | 16 | 29.77 | 17 |
| 3.600 | 30.15 | 8 | 30.50 | 9 |

FIG. 3 also includes SEM microphotographs that show the particles before and after the solvent exchange procedure. As indicated, the solvent exchange resulting in particles containing a porous network that includes a plurality of nanopores.

Example 23

Particles were formed in a manner as described in U.S. Pat. No. 8,742,023 to Fujimura, et al. and had an initial Vortex Time of 35 seconds and CRC of about 27.5 g/g. The particles were sieved to 600-1,000 microns and then downsized using blender and sieved again to collect 300-600 microns.

Example 24

Particles were formed in a manner as described in U.S. Pat. No. 8,742,023 to Fujimura, et al. and had an initial Vortex Time of 35 seconds and CRC of about 27.5 g/g. The particles were treated with a solvent and then washed with a non-solvent as described herein to create voided superabsorbent particles. The particles were then sieved to 600-850 microns and downsized using blender and sieved again to collect 300-600 microns.

Samples from Example 23 and Example 24 were tested for specific surface area (B. E. T.) in accordance with ISO 9277:2010. The results are set forth below.

| Example | B.E.T. Surface Area (m$^2$/g) |
|---|---|
| 23 | 0.16 |
| 24 | 2.43 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. Superabsorbent particles having a median size of from about 50 to about 2,000 micrometers and containing nanopores having an average cross-sectional dimension of from about 10 to about 500 nanometers, wherein the superabsorbent particles exhibit a Vortex Time of about 80 seconds or less.

2. The superabsorbent particles of claim 1, wherein the particles exhibit an Absorption Rate of about 300 g/g/ks or more after being placed into contact with an aqueous solution of 0.9 wt. % sodium chloride for 0.015 kiloseconds.

3. The superabsorbent particles of claim 1, wherein the superabsorbent particles exhibit an Absorption Rate of about 500 g/g/ks or more after being placed into contact with an aqueous solution of 0.9 wt. % sodium chloride for 0.015 kiloseconds.

4. The superabsorbent particles of claim 1, wherein the superabsorbent particles exhibit an Absorption Rate of about 160 g/g/ks or more after being placed into contact with an aqueous solution of 0.9 wt. % sodium chloride for 0.120 kiloseconds.

5. The superabsorbent particles of claim 1, wherein the superabsorbent particles exhibit a total absorbent capacity of about 10 g/g or more after being placed into contact with an aqueous solution of 0.9 wt. % sodium chloride for 3.6 kiloseconds.

6. The superabsorbent particles of claim 1, wherein the particles exhibit a Centrifuge Retention Capacity of about 20 g/g or more.

7. The superabsorbent particles of claim 1, wherein the particles further contain micropores.

8. The superabsorbent particles of claim 1, wherein the nanopores constitute at least about 25 vol. % of pores in the particles.

9. The superabsorbent particles of claim 1, wherein the particles are formed from a crosslinked polymer that contains repeating units derived from one or more ethylenically unsaturated monomeric compounds having at least one hydrophilic radical.

10. The superabsorbent particles of claim 9, wherein the monomeric compounds are monoethylenically unsaturated.

11. The superabsorbent particles of claim 9, wherein the hydrophilic radical includes a carboxyl, carboxylic acid anhydride, carboxylic acid salt, sulfonic acid, sulfonic acid salt, hydroxyl, ether, amide, amino, quaternary ammonium salt group, or a combination thereof.

12. The superabsorbent particles of claim 9, wherein the polymer contains repeating units derived from a (meth) acrylic acid monomeric compound or a salt thereof.

13. The superabsorbent particles of claim 9, wherein the polymer contains an alkoxysilane functionality.

14. The superabsorbent particles of claim 1, wherein the particles exhibit a total pore area of about 2 square meters per gram or more.

15. The superabsorbent particles of claim 1, wherein the particles exhibit a percent porosity of about 5% or more.

16. The superabsorbent particles of claim 1, wherein the particles exhibit a bulk density of less than about 0.7 grams per cubic centimeter as determined at a pressure of 0.58 psi via mercury intrusion.

17. The superabsorbent particles of claim 1, wherein the particles have an average pore diameter of from about 1 to about 1,200 nanometers.

18. The superabsorbent particles of claim 1, wherein the particles have a specific surface area of about 0.2 square meters per gram or more as determined in accordance with ISO 9277:2010.

19. A method for forming the superabsorbent particles of claim 1, the method comprising:
   forming a composition that contains a superabsorbent polymer and a solvent system; and
   contacting the composition with a non-solvent system to initiate formation of pores through phase inversion.

20. The method of claim 19, further comprising removing non-solvent from the composition.

21. The method of claim 19, wherein the composition is a single-phase homogeneous composition.

22. The method of claim 19, wherein contact with the non-solvent system forms a two-phase mixture.

23. The method of claim 19, wherein the difference in the Hildebrand solubility parameter of the solvent system and the Hildebrand solubility parameter of the non-solvent system is from about 1 to about 15 calories$^{1/2}$/cm$^{3/2}$.

24. The method of claim 19, wherein the solvent system includes water, aqueous alcohol, saline, or a combination thereof.

25. The method of claim 19, wherein the non-solvent system includes acetone, n-propyl alcohol, ethyl alcohol, methanol, n-butyl alcohol, propylene glycol, ethylene glycol, or a combination thereof.

* * * * *